United States Patent [19]

Rodrian

[11] 4,247,758
[45] Jan. 27, 1981

[54] ANIMAL IDENTIFICATION AND ESTRUS DETECTION SYSTEM

[76] Inventor: James A. Rodrian, 1123 Lake Shore Rd., Grafton, Wis. 53024

[21] Appl. No.: 94,750

[22] Filed: Nov. 15, 1979

Related U.S. Application Data

[63] Continuation of Ser. No. 963,456, Nov. 24, 1978, abandoned.

[51] Int. Cl.³ .................... G07C 11/00; H04Q 9/00
[52] U.S. Cl. .............................. 235/92 MS; 119/1; 235/92 PL; 340/152 T
[58] Field of Search ........ 235/92 MS, 92 MP, 92 PL, 235/92 CC; 340/152 T; 119/1

[56] References Cited

U.S. PATENT DOCUMENTS

| | | | |
|---|---|---|---|
| 3,304,911 | 2/1967 | Hakata et al. | 119/1 |
| 3,378,675 | 4/1968 | Cromley | 235/92 MS |
| 3,494,329 | 2/1970 | Frieberger et al. | 119/1 |
| 3,540,413 | 11/1970 | Castaigne | 119/1 |
| 3,633,001 | 1/1972 | Vajnovszky | 235/92 MS |
| 3,803,571 | 4/1974 | Luz | 119/1 |
| 3,844,273 | 10/1974 | Polson | 119/1 |
| 4,112,926 | 9/1978 | Schulman et al. | 235/92 PL |

Primary Examiner—Joseph M. Thesz
Attorney, Agent, or Firm—Quarles & Brady

[57] ABSTRACT

An animal such as a dairy cow carries a transponder unit which includes a motion sensor. When the animal comes within range of a transceiver unit, it is interrogated and the transponder unit transmits data which identifies the animal and indicates the number of movements of the animal. The number of animal movements increase dramatically during estrus and a record is kept on each animal to determine when this occurs. Data received at the transceiver is processed by a microprocessor based system which operates to insure the received data is correct. It also assembles the data and outputs it to a printer.

10 Claims, 6 Drawing Figures

ANIMAL IDENTIFICATION AND ESTRUS DETECTION SYSTEM

This is a continuation of application Ser. No. 963,456, filed Nov. 24, 1978, now abandoned.

BACKGROUND OF THE INVENTION

The field of the invention is automatic systems for indicating estrus in animals, and more particularly, systems for electronically indicating estrus in dairy cows.

The accurate detection of estrus in animals is a significant factor in reproductive efficiency where artificial insemination is used. When applied to dairy cows, accurate detection of estrus is an important factor in determining the total milk production of the herd. A number of estrus, or heat, detection methods are presently used, but by far the most widely used method is to observe either manually or with a video recorder, the activity of the cow. In a large dairy herd this practice becomes difficult and inefficient.

As reported in the *Journal of Dairy Science* Vol. 60, No. 2 by Charles A. Kiddy of the U.S. Department of Agriculture, cows are appreciably more active at estrus than at other times during the estrus cycle. This was confirmed by tests run in which pedometers were attached to the hind leg of a number of cows and their activity was monitored over a period of time. In these tests the pedometer counted the number of leg movements and the pedometer was visually read twice a day when the cow was milked. The number of counts at each reading were found to increase by a factor of three or more during estrus.

SUMMARY OF THE INVENTION

The present invention relates to an electronic system for detecting estrus in animals in which a transponder carried by the animal counts the number of body movements of the animal during a selected time period and this activity count along with an animal identification number is transmitted to a transceiver unit where the data is processed and stored. More particularly, the electronic system includes a transponder attached to the animal which contains a motion detector, a digital counter, means for storing a preselected animal identification number and means responsive to an interrogation signal received from a transceiver for transmitting the activity count and the animal identification number to the transceiver. The transceiver incudes means for generating the interrogation signal and means for receiving, decoding and visually displaying the activity count and the animal identification number transmitted by the transponder.

The transponder unit is attached to the animal and the transceiver unit is positioned at a location which the animal periodically frequents. When applied to dairy cows, for example, the transponder may be in the form of a tag which is attached to a chain around the animal's neck. The transmit and receive coils of the transceiver may be positioned at the entrance to the milking parlor. In the early morning and evening the cow enters the milking parlor and passes by the transceiver coils. The transponder carried by the animal is interrogated and the identity of the cow along with the activity count, which indicates the number of substantial movements of the animal during the preceeding time period, is transmitted by the transponder and received at the receive coil. These numbers are recorded and the farmer may easily review them periodically to determine which cows are unusually active.

A general object of the invention is to provide a practical electronic system for detecting estrus in animals. The transponders must be low in cost, mechanically rugged and electrically reliable. Obviously the surroundings in which the system will operate demands that special measures be taken to insure proper operation over a wide temperature range, in an electrically noisy environment, and after repeated, sever physical shock. In addition, the economic environment requires that the system be competitive in cost with other methods of estrus detection.

A more specific object of the invention is to add estrus detection to the animal identification system disclosed in my co-pending U.S. patent application Ser. No. 815,796 filed July 15, 1977 and entitled "Animal Identification System," now U.S. Pat. No. 4,129,855.

The foregoing and other objects and advantages of the invention will appear from the following description. In the description reference is made to the accompanying drawings which form a part thereof, and in which there is shown by way of illustration a preferred embodiment of the invention. Such description does not necessarily represent the full scope of the invention, and reference is made to the claims herein for interpreting the breadth of the invention.

DESCRIPTION OF THE PREFERRED EMBODIMENT

The system of the present invention employs the concept and much of the identical circuitry disclosed in my co-pending Animal Identification System patent application cited above and the disclosure of that co-pending application is hereby incorporated by reference.

Figure 1:
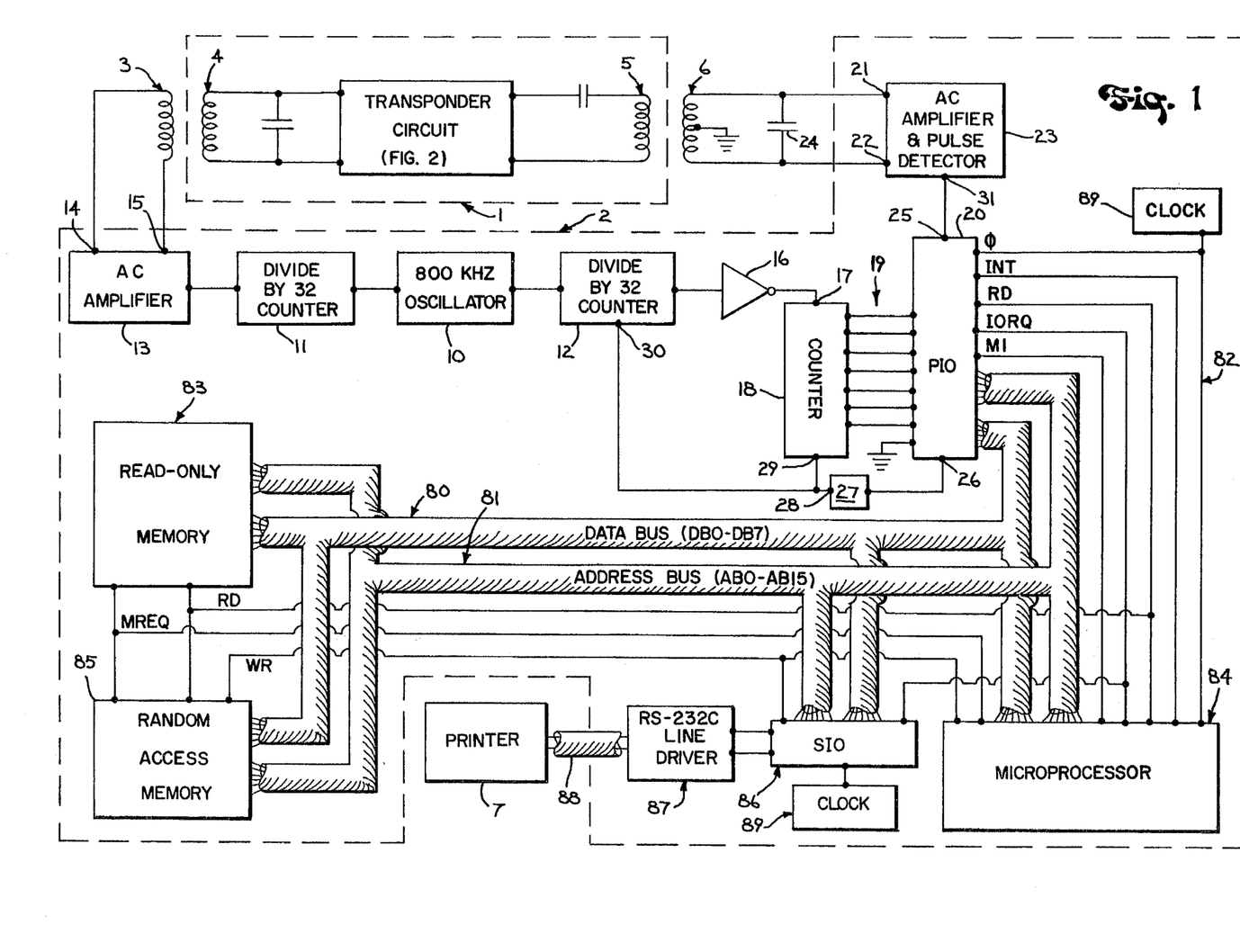
FIG. 1 is an electrical schematic diagram of the estrus detection system of the present invention.

Referring to FIG. 1, the system of the present invention includes a transponder unit indicated by the dashed lines 1 which is enclosed in a molded plastic case (not shown in the drawings) and which is attached to a chain that hangs around the neck of the animal. The system also includes a transceiver unit indicated by the dashed line 2 which is housed in an enclosure and positioned near the location which the animal frequents. When the animal approaches the vicinity of the transceiver unit 2, the transponder unit 1 carried by the animal is interrogated by an electromagnetic signal generated by a count transmitter coil 3 which is connected to the transceiver 2. The transponder unit 1 includes a count receive coil 4 and the transponder unit 1 is responsive to the interrogation signal to generate a series of reset pulses at a reset pulse transmitter coil 5 which indicate both the identity of the animal and the activity count of the animal. The reset pulses generated by the transponder unit 1 are received by a reset pulse receive coil 6 which connects to the transceiver unit 2. As will be described in more detail below, the transceiver unit 2 operates to decode the reset pulses to provide an animal identification number and an animal activity number which are generated in digital form to a character printer 7.

Figure 5:
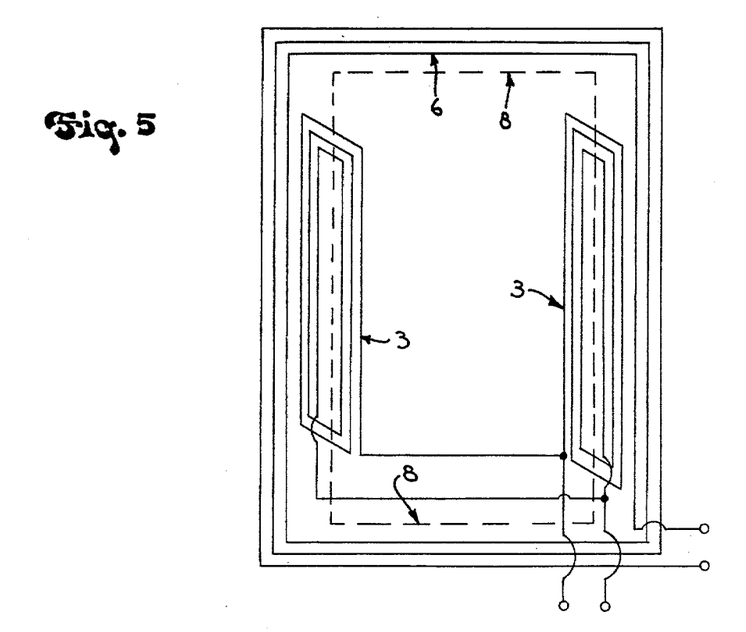
FIG. 5 is a schematic representation of the physical arrangement of the transceiver transmit and receive coils which form part of the system of FIG. 1.

The physical construction of the transponder unit 1 including its count receive coil 4 and its reset pulse transmitter coil 5 is discussed in detail in my above cited co-pending patent application. In the present embodiment of the invention, however, the count transmitter coil 3 and the reset pulse receive coil 6 associated with the transceiver unit 2 are not located at individual feeding stations as disclosed in my prior application, but are instead, located at the entrance to the milking parlor. Referring particularly to FIG. 5, the count transmitter coil 3 and the reset pulse receive coil 6 are significantly larger and are attached to a door frame 8 which surrounds the entrance to the milking parlor. The coils 3 and 6 form an archway through which the animals pass on the way to the milking parlor and it is at this moment that the transponder unit 1 carried by the animal is interrogated and the animal activity count and animal identification number are conveyed to the transceiver unit 2. The physical characteristics of the count transmitter coil 3 and the reset pulse receive coil 6 are provided in Table A.

TABLE A

| | |
|---|---|
| Count transmitter coil 3 | 25 turns of #28 AWG wire, each turn defining an area of approximately 232 square inches. |
| Count receive coil 4 | 500 turns of #36 AWG wire, each turn defining an area of approximately 4.8 square inches. |
| Reset pulse transmitter coil 5 | 100 turns of #36 AWG wire, each turn defining an area of approximately 2.24 square inches. |
| Reset pulse receive coil 6 | 6 turns of #22 AWG wire, each turn defining an area of approximately 16.0 square feet. |

Referring again to FIG. 1, the transceiver unit 2 employs the concept disclosed in my above cited co-pending patent application. It includes an oscillator 10 which generates 800 kHz clock pulses to the input of a first divide by thirty-two counter 11 and to the input of a second divide by thirty-two counter 12. The output of the first counter 11 is a 25 kHz pulse train which is applied to the input of an a.c. amplifier 13. A pair of output terminals 14 and 15 on the a.c. amplifier 13 connect to the count transmitter coil 3, and the count transmitter coil 3 thus generates a continuous, unmodulated 25 kHz interrogation signal.

The output of the second divide by thirty-two counter 12 connects through an inverter gate 16 to the clock terminal 17 of a seven stage ripple counter 18. The counter 18 is thus incremented at a rate of 25 kHz in synchronizm with the 25 kHz signal generated by the count transmitter coil 3. The resulting count at any point in time appears at a set of seven output terminals which connect through leads 19 to the input port of a parallel input/output circuit (PIO) 20.

The transponder unit 1 is responsive to the 25 kHz signal generated by the count transmitter coil 3 to generate reset pulses to the reset pulse receive coil 6 which connects to the transceiver 2. Each reset pulse is a burst of 200 kHz electromagnetic energy which is applied to the inputs 21 and 22 of an a.c. amplifier and pulse detector 23. A capacitor 24 connects across the coil 6 to tune it to 200 kHz. The 200 kHz burst is amplified by the amplifier 23 and a reset pulse of approximately 20 microsecond duration is formed therefrom and generated at a detector output terminal 31. This detected reset pulse is applied to an STB terminal 25 on the PIO 20 and the binary number stored in the counter 18 at that moment is gated into and stored in the PIO 20. The PIO 20 also responds by generating a logic high voltage at a RDY terminal 26 and this voltage is applied to the input of a monostable multivibrator circuit 27. The Q output 28 on the monostable multivibrator circuit 27 connects to a reset terminal 29 on the counter 18 and to a reset terminal 30 on the divide by thirty-two counter 12.

The operation of the transceiver circuitry thus far described is virtually identical to the operation of the transceiver circuit described in my above cited co-pending patent application. The oscillator 10 is continuously running and the ripple counter 18 is thus continuously incremented. When no transponder unit 1 is in the vicinity of the transceiver coils 3 and 6, the ripple counter 18 repeatedly counts out and resets to zero, but its output is not entered into the PIO 20. When an animal carries a transponder unit 1 into range, however, the transponder unit 1 generates reset signals to the transceiver coil 6. The first reset pulse formed from the reset signals is applied to the PIO 20 and the contents of the ripple counter 18 is loaded into the PIO 20. More importantly, however, the first reset pulse resets the counter 18 to zero to synchronize it with a similar counter in the transponder unit 1 as taught by my prior patent application. The ripple counter 18 continues to be incremented by the oscillator 10, and as subsequent reset signals are received from the transponder unit 1, the contents of the counter 18 are inputted to the PIO 20 and the counter 18 is reset. A series of four-bit binary numbers are thus entered into the PIO 20 after the counter 18 is synchronized with the transponder 1. This series of four-bit bytes includes a flag byte, four data bytes which identify the animal carrying the transponder unit 1, and two data bytes which indicate the activity of the animal.

The transceiver unit 2 continuously interrogates the transponder unit 1 when it is within range of the count transmitter coil 3. The animal identification number and activity number are received repeatedly as the animal enters the milking parlor. As will be described in more detail hereinafter, noise immunity is achieved by requiring that four identical series of animal identification and animal activity bytes are received by the PIO 20 before the data is acknowledged to be valid and is acted upon.

Figure 2:
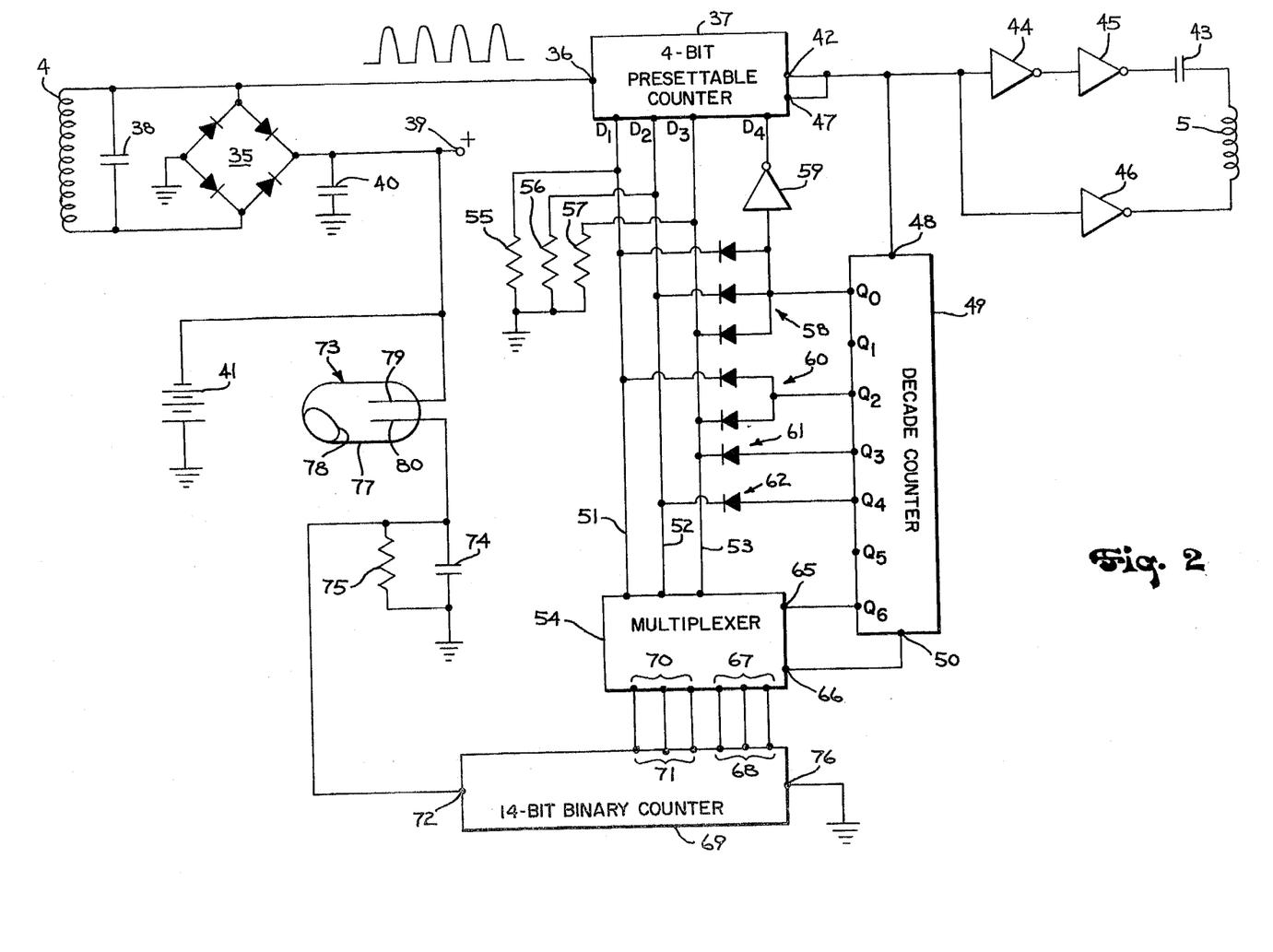
FIG. 2 is an electrical schematic diagram of the transponder unit which forms part of the system of FIG. 1.

Referring particularly to FIG. 2, the transponder unit 1 of the present invention employs the concept disclosed in my above cited co-pending patent application, but because both an identification number and an activity number are involved, the particular circuitry is different.

The interrogation signal received at the count receive coil 4 is applied across the input terminals of a full-wave bridge rectifier circuit 35. A capacitor 38 is connected in parallel with the count receive coil 4 and its value is selected to tune the resulting tank circuit to 25 kHz. One output terminal on the rectifier circuit 35 is connected to signal ground and its other output connects to a positive d.c. supply terminal 39. A filter capacitor 40 also connects to the positive d.c. supply terminal 39 as does a 5.6 volt battery 41.

One lead of the coil 4 is also connected directly to the clock terminal 36 of a four-bit presettable counter 37. When a 25 kHz interrogation signal is received at the transponder coil 4, it is rectified by the circuit 35 and the positive portion of each cycle is applied to the clock terminal 36 of the counter 37. The four-bit presettable counter 37 is preset to a selected count through a set of four terminals $D_1$, $D_2$, $D_3$ and $D_4$ and it is counted down by the rectified 25 kHz interrogation signal. When the counter 37 is counted down to zero, a logic high voltage is generated at an output terminal 42 which is applied to its own preset enable terminal 47.

This logic high voltage is also applied to the input of an inverter oscillator circuit which includes the reset pulse transmitter coil 5, a capacitor 43 and a set of three inverter gates 44–46. The series resonant circuit formed by the reset pulse transmitter coil 5 and the capacitor 43 is tuned to 200 kHz, and each time the output of the four-bit presettable counter 37 goes high, a burst of 200 kHz energy is inductively coupled by the reset pulse transmitter coil 5 to the transceiver unit 2. After the first such reset signal is transmitted, the presettable counter 37 becomes synchronized with the counter 18 in the transceiver unit 2. During subsequent intervals between reset signals, therefore, the counter 37 is counted down from a preset four-bit binary number and the counter 18 is counted up to the very same number. In this manner, a series of four-bit binary numbers loaded into the presettable counter 37 through its terminals $D_1$–$D_4$ are effectively transmitted to the transceiver unit 2 and loaded into the PIO 20.

The output terminal 42 of the four-bit presettable counter 37 is also connected to a clock terminal 48 on a decade counter 49. The decade counter 49 includes ten output terminals $Q_0$–$Q_9$ and a carry output terminal 50. The decade counter 49 is employed as a ring counter in which a logic high voltage is advanced along the output terminals $Q_0$–$Q_9$ each time a logic high voltage is received at the clock terminal 48. That is, a "one" appears at the output $Q_0$ and is shifted to the output $Q_1$ when a logic high voltage is applied to the clock terminal 48. It is shifted to the output terminal $Q_2$ when another logic high voltage is applied to the clock terminal 48, and it is advanced through the remaining outputs $Q_3$–$Q_9$ as subsequent signals are applied to the clock terminal 48. When the "one" reaches the output $Q_5$ a logic high voltage is generated at the carry terminal 50 and this terminal remains at a logic high voltage until the "one" is shifted through the remaining outputs $Q_6$–$Q_9$ back to the output terminal $Q_0$.

The decade counter 49 serves to sequentially apply four-bit bytes of data to the present terminals $D_1$–$D_4$ on the counter 37. The preset inputs $D_1$–$D_3$ connect through a set of lines 51–53 to the outputs of a three channel, two-line-to-one-line multiplexer 54 and to a set of three pull down resistors 55–57. The preset inputs $D_1$–$D_3$ are thus held at a logic low voltage by the resistors 55–57 unless a logic high voltage is applied to them by the multiplexer circuit 54 or by the decade counter 49 through selectively connected diodes.

For example, the $Q_0$ output on the decade counter 49 is connected through a set of three diodes 58 to the respective preset input terminals $D_1$–$D_3$ and through an inverter gate 59 to the preset input terminal $D_4$. When the "one" circulated by the decade counter 49 appears at the $Q_0$ output terminal, the preset terminals $D_1$–$D_3$ are driven to a logic high voltage and the preset terminal $D_4$ is driven low. The four-bit presettable counter 37 is thus preset to the number seven and a logic high voltage will not be generated at the counter output terminal 42 until seven 25 kHz pulses have been applied to its clock terminal 36. When this occurs the decade counter 49 is advanced to generate its "one" at the $Q_1$ output terminal. This first byte of data (i.e., the number seven) serves as a flag byte which identifies the beginning of the sequence of bytes to follow.

The following four outputs $Q_1$–$Q_4$ on the decade counter 49 are "programmed" by means of diodes 60–62 to generate four bytes of data which comprise a unique identification number. In the preferred embodiment shown in FIG. 2, the $Q_1$ output is not connected to any of the lines 51–53, the $Q_2$ output is connected through diodes 60 to lines 51 and 53, the $Q_3$ output is connected through a diode 61 to the line 53 and the $Q_4$ is connected through a diode 62 to the line 52. As the "one" is advanced through the decade counter output terminals $Q_1$–$Q_4$, therefore, the digits "zero," "five," "four," and "two" (i.e., I.D. No. 1320) are sequentially applied to the preset input terminals $D_1$–$D_3$ on the presettable counter 37 and effectively coupled to the transceiver 2. It should be apparent to those skilled in the art that by selectively connecting diodes between the decade counter output terminals $Q_1$–$Q_4$ and the three lines 51–53 that any animal identification number from 0 to 4095 can thus be programmed.

After the decade counter 49 has been advanced through its outputs $Q_0$–$Q_4$ and the flag byte and the four animal identification bytes have been coupled to the transceiver unit 2, the "one" is advanced through the counter outputs $Q_5$ and $Q_6$. When this occurs two three-bit bytes of a six-bit "activity number" are applied to the presettable counter 37. More specifically, the $Q_6$ output of the decade counter 49 is connected to the select terminal 65 on the multiplexer 54 and the carry output terminal 50 on the decade counter 49 is connected to the enable terminal 66 on the multiplexer 54. Three input terminals 67 on the multiplexer 54 connect to the three most significant digit output terminals 68 on a fourteen-bit binary counter 69 and the second set of three input terminals 70 on the multiplexer 54 connect to the next three most significant digit output terminals 71 on the binary counter 69.

When the "one" in the decade counter 49 is generated at its $Q_5$ output terminal, a logic high voltage is generated at its carry output terminal 50 and is applied to enable the multiplexer circuit 54. The multiplexer select terminal 65 is at a logic low voltage, and as a result, the three least significant digits of the six most significant digits stored in the fourteen-bit binary counter 69 are coupled through the multiplexer input terminals 70 on the lines 51–53 which drive the preset inputs $D_1$–$D_3$ on the presettable counter 37. After that three-bit number has been counted down to zero by the counter 37, the "one" in the decade counter 49 is advanced to the $Q_6$ output terminal and the select terminal 65 on the multiplexer 54 is driven to a logic high voltage. As a result, the three most significant digits stored in the fourteen-bit binary counter 69 are coupled through the multiplexer inputs 67 to the lines 51–53 and are applied to the preset inputs $D_1$–$D_3$ on the presettable counter 37. A six-bit binary coded activity number is thus indicated to the transceiver 2 following its receipt of the flag byte and the animal identification number.

The fourteen-bit binary counter 69 is driven by a motion sensing device which generates a logic high voltage to a clock input terminal 72 each time the animal carrying the transponder unit 1 makes a significant movement. More specifically, one lead of a mercury switch 73 connects to the clock terminal 72 through a filter comprised of capacitor 74 and resistor 75. The other lead on the mercury switch 73 connects to the positive d.c. supply terminal 39 and a reset terminal 76 on the fourteen-bit binary counter 69 is connected to signal ground. The mercury switch 73 is a commercially available product which includes a glass envelope 77 that contains a bead of mercury 78.

The transponder unit 1 is preferably attached to a chain around the animal's neck, and as the animal walks, the transponder unit 1 swings. The bead of mercury 78 is thrown about within the envelope 77 by this swinging motion and it opens and closes the switch 73 by bridging across two stationary terminals 79 and 80. Each time the switch 73 is closed, a logic high pulse is applied to the fourteen-bit binary counter 69 and the fourteen-bit binary number stored therein is incremented one count. The fourteen-bit binary counter 69 is thus continuously incremented and when the animal approaches the vicinity of the transceiver 1, the six most significant digits of the counter 69 are read out and coupled to the transceiver 1. The binary counter 69 is not reset after each reading, but is instead, automatically reset to zero when it reaches its maximum count.

To summarize the operation of the system, when the transponder unit 1 comes within range of the transceiver unit 2, interrogation pulses are applied to the four-bit presettable counter 37 in the transponder unit 1. These 25 kHz pulses are simultaneously applied to the counter 18 in the transceiver unit 2. These two counters become synchronized with one another after the presettable counter 37 is counted down to zero and the first reset pulse is generated back to the transceiver unit 2. The presettable counter 37 is immediately preset with another number and as it is counted down to zero by the 25 kHz pulses, the counter 18 in the transceiver unit 2 is synchronously counted up from zero. At the moment the presettable counter 37 reaches zero and transmits a reset pulse back to the transceiver 2, the counter 18 has reached the same count which was preset into the presettable counter 37. This count is loaded into the PIO 20 and processed by the microprocessor system now to be described. In this manner, the four-bit bytes of data applied to the preset input terminals $D_1$-$D_4$ of the presettable counter 37 are sequentially loaded into the PIO 20 and processed to form an animal identification number and an animal activity number. The number "seven" applied to the presettable counter 37 when the "one" is generated at the $Q_0$ output of the decade counter 49 serves as a flag, or keying byte. That is, the four data bytes which follow this keying byte constitute the animal identification number and the next two data bytes constitute the activity number.

While the transponder 1 is within range of the transceiver 2, the system continuously cycles through the sequence of coupling the flag byte, the four animal identification bytes, the two animal activity bytes, and the three unused bytes (i.e., outputs $Q_7$-$Q_9$ of the decade counter 49). It is one of the features of the present invention that this data is not acted upon until four identical cycles are received. As a result, the system is relatively immune from electrical noise commonly found in the farm environment which may otherwise disturb the transmission and reception of a single byte.

Referring to FIG. 1, the four-bit bytes of data sequentially loaded into the PIO 20 are processed by a microprocessor based system which is structured around an eight-bit data bus 80 and a sixteen-bit address bus 81. A model number Z-80 microprocessor manufactured by Zilog is employed and it is directly coupled to the PIO 20 through the data bus 80, the address bus 81 and a set of control lines indicated generally at 82. The timing of the system elements is coordinated by a single phase clock 89 which operates at 2 MHz. An eight-bit by 2K read-only memory 83 is also connected to the microprocessor 84 through the buses 80 and 81 and through selected control lines. Similarly, an eight-bit by 512 line random access memory 85 is coupled to the microprocessor 84. The read-only memory 83 stores the machine instructions which are executed by the microprocessor 84 to carry out the data processing functions which will be described hereinafter, and the random access memory 85 stores data which is operated upon during processing.

A serial I/O controller (SIO) 86 driven by a 1200 kHz clock 89 also connects to the data bus 80 and the address bus 81. The SIO 86 is coupled through an RS-232-C line driver 87 to an alpha-numeric printer 7 and when the SIO circuit 86 is addressed through the bus 81 and enabled through control lines WR and IORQ, it outputs a seven-bit ASCII character to the printer 7. The interface circuit 87 operates to generate the seven-bit ASCII character serially over a line 88 and this line may be up to 50 feet in length. The printer 7 may therefore, be located remotely from the transceiver unit 2, which is particularly advantageous in a farm environment.

The microprocessor 84 sequentially reads machine instructions out of the read-only memory 83, and in response to operation codes in these instructions, it performs a number of functions. These functions include reading in bytes of data from the PI0 20, performing calculations on such data and writing partial results into the random access memory 85. The ultimate results of these calculations, the animal identification number and animal activity number, are outputed to the printer 7.

For a more detailed description of the instruction set employed by the microprocessor 84 and the manner in which the microprocessor 84 operates the PIO 20, the SIO 86 and the memories 83 and 85, reference is made to the *Z80-CPU Technical Manual published in* 1976 by Zilog.

The detailed functions performed by the data processor system is best explained with reference to the flow charts shown in FIGS. 3 and 4. These flow charts represent the functions carried out by the microprocessor 84 in response to machine instructions stored in the read-only memory 83, and for a detailed listing of these machine instructions, reference is made to Appendix A.

Figure 3:
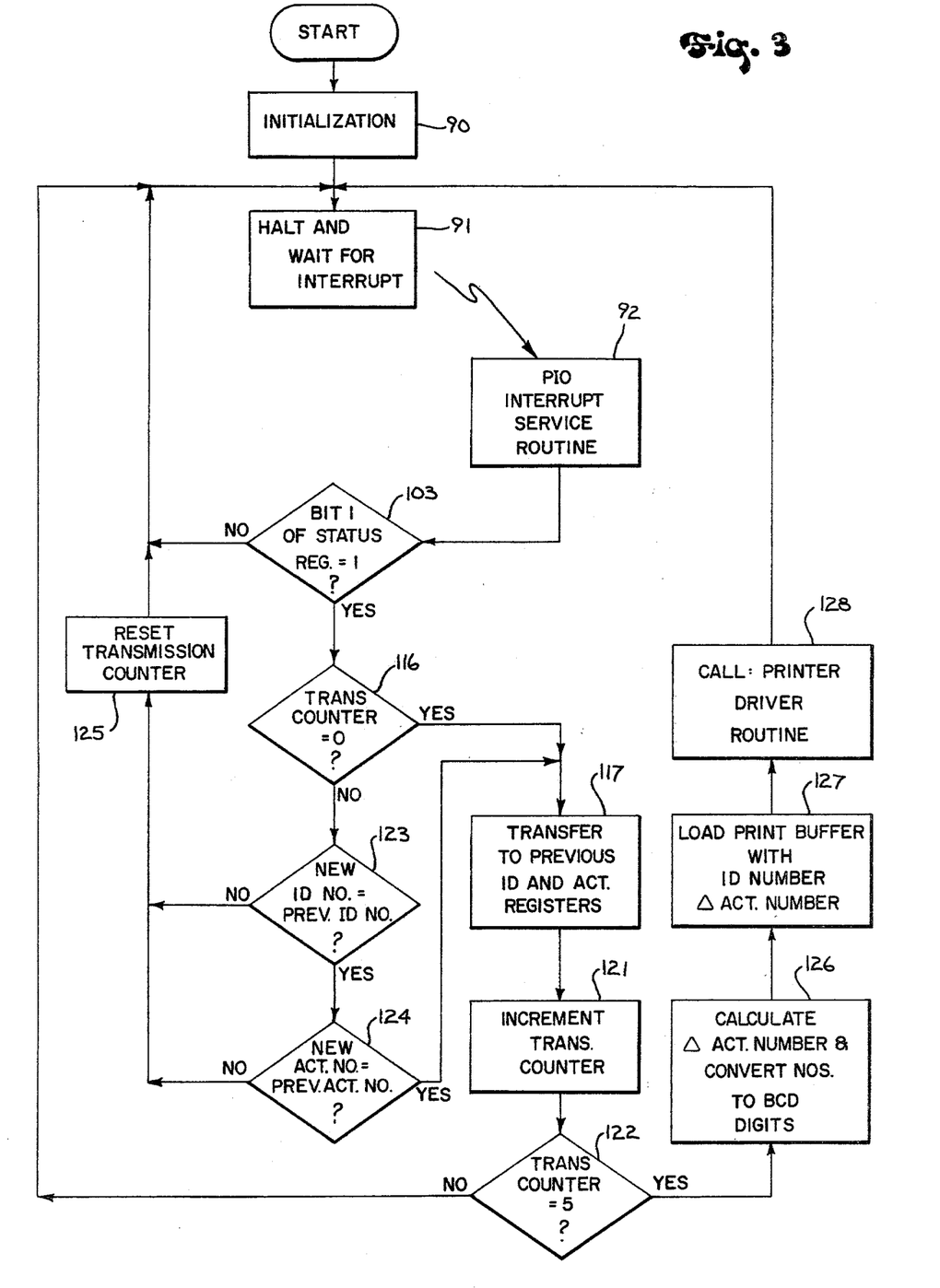
FIG. 3 is a flow chart of the system software executed by the microprocessor which forms part of the system of FIG. 1.
Figure 4:
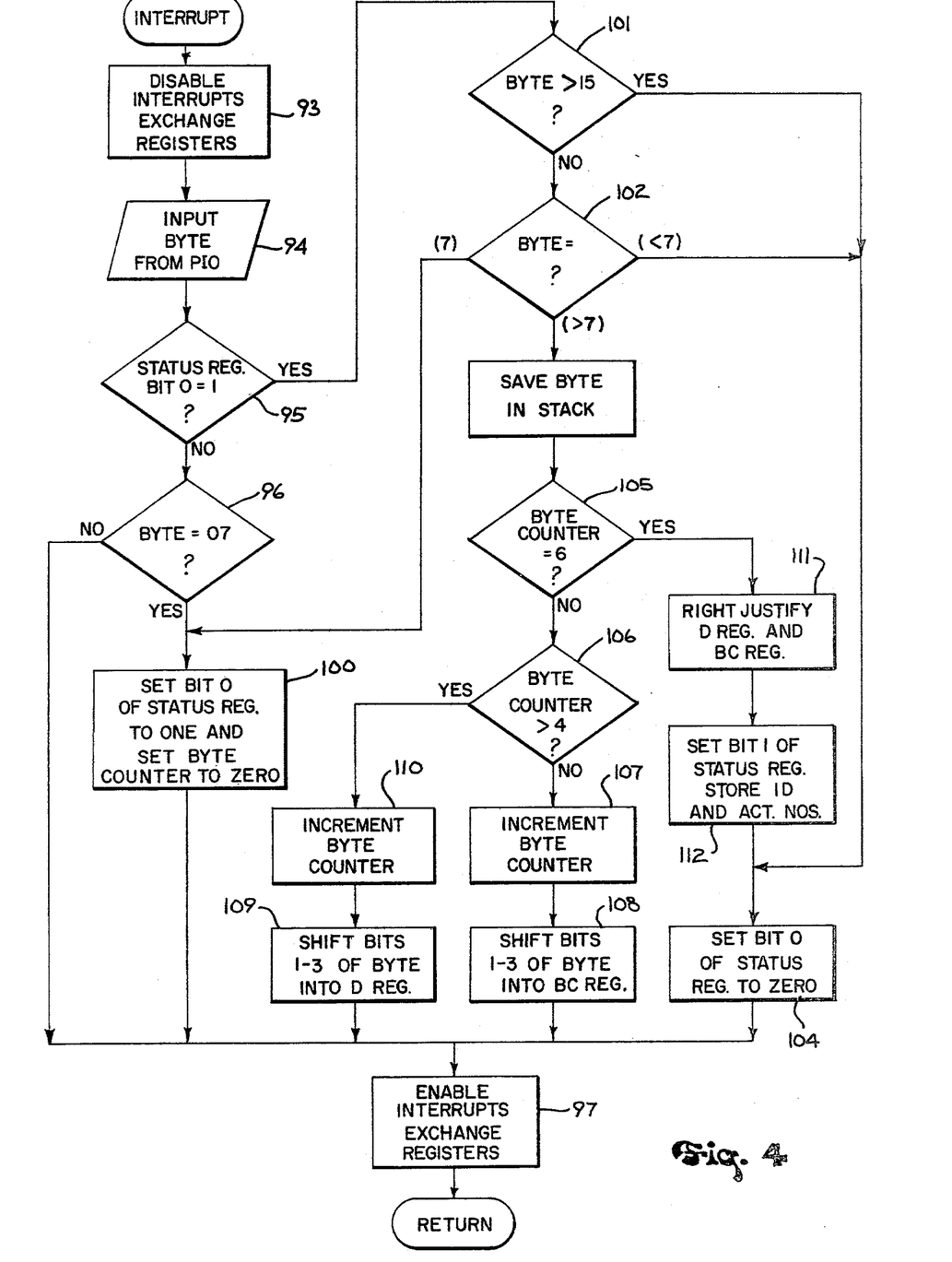
FIG. 4 is a flow chart of the PIO interrupt service routine which forms part of the system software of FIG. 3.

Referring particularly to FIG. 3, after the microprocessor 84 executes a series of instructions which initialize the system as indicated by process block 90, the system halts and waits for an interrupt as indicated by a process block 91. When a byte of data is loaded into the PIO 20, an interrupt request is generated to the microprocessor 84 and the system is vectored, or jumped, to a PIO interrupt service routine indicated in FIG. 3 by a process block 92. A flow chart of the PIO interrupt service routine 92 is shown in FIG. 4 and this flow chart will now be described in conjunction with the memory map of the random access memory 85 shown in FIG. 6.

Figure 6:
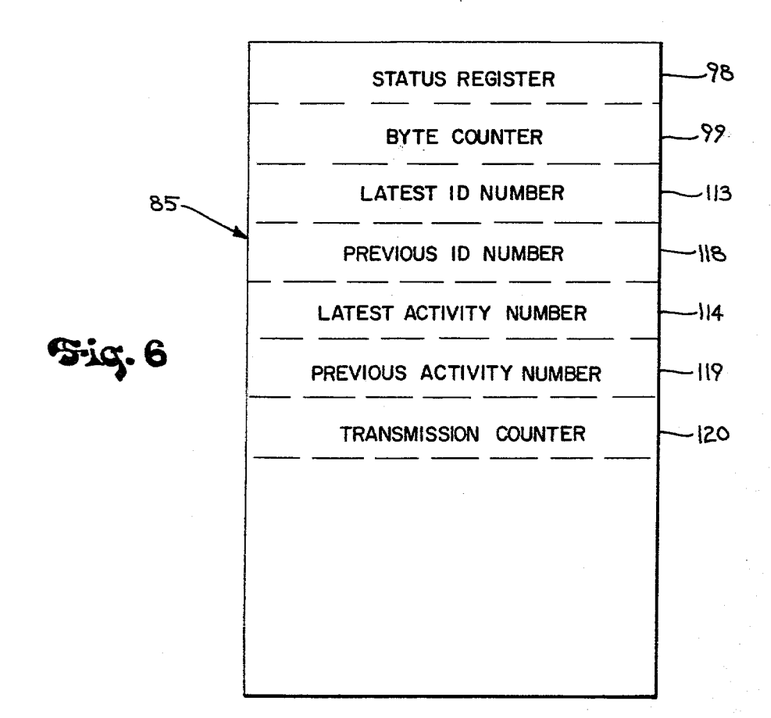
FIG. 6 is a memory map of the contents of a random access memory which forms part of the system of FIG. 1.

The PIO interrupt service routine first disables further interrupts and then saves the contents of the microprocessor registers as indicated by process block 93. The eight-bit byte of data from the PIO 20 is then input to the microprocessor 84 as indicated by input block 94 and the least significant bit (i.e., bit zero) of a status register 98 stored in the random access memory 85 is then examined as indicated by decision block 95 to determine if it is equal to one. This particular bit in the status register 98 indicates whether or not the flat byte has previously been received from a transponder, and if it has, the value of the presently received byte is determined as indicated by decision blocks 101 and 102. On the other hand, if bit zero of the status register 98 is not equal to one, the presently received byte is examined, as indicated by decision block 96, to determine whether it is the flag byte. If it is not, the data is meaningless and the routine returns through a set of instructions indicated by process block 97. But if it is the flag byte, bit zero of the status register 98 is set to "one" and a byte counter 99 also stored in the random access memory 85 is set to zero. The machine instructions which accomplish these functions are indicated collectively in FIG. 4 by a process block 100. After these functions are completed the system returns through the process block 97 which includes instructions that enable further interrupts and reloads the microprocessor registers with the data they contained when the PIO interrupt service was first entered.

Referring again to FIG. 3, when the system returns from the PIO interrupt service routine instructions indicated by decision block 103 are executed to determine if bit 1 of the status register 98 has been set to one. As will be explained below, this does not occur until the flag byte, four bytes of the animal identification number and two bytes of the activity number are successfully received. Consequently, until all of this data is received, the system branches back to the process block 91 and awaits the next interrupt from the PIO 20.

Referring again to FIG. 4, when the next byte of data is input from the PIO 20 it is examined by instructions indicated by decision blocks 101 and 102 to determine its value. If it has a value greater than 15 as determined by decision block 101, an error has occurred and the system branches to a set of instructions indicated by a process block 104. These instructions reset bit zero of the status register to zero, and as a consequence, another flag byte must be received and the sequence restarted. Similarly, if the received byte is less than seven as determined by decision block 102, an error has occurred and the system branches back through process block 104 and process block 97. If on the other hand, the value of the data byte is greater than seven it is valid data and it is saved in a microprocessor "stack."

Instructions indicated by decision blocks 105 and 106 are then executed to determine which of the six data bytes it is. This is determined by examining the value of the byte counter 99 stored in the random access memory 85. If the byte counter is less than four as determined by decision block 106, the data is part of the animal identification number. In such case the byte counter 99 is incremented one count as indicated by process block 107 and the three least significant bits of the received byte are shifted into the upper end of the microprocessor B and C registers (not shown in the drawings). The system returns through the process block 97 and awaits the receipt of the next interrupt from the PIO 20.

After the four bytes which comprise the animal identification number have been received and shifted into the microprocessor B and C registers, the byte counter is greater than four when the system reaches decision block 106. The next two bytes of data are the activity number and these are shifted into the microprocessor D register (not shown in the drawings) as indicated by process block 109. The byte counter 99 is incremented as indicated by process block 110 and when it reaches the value of six, as determined during the next interrupt by decision block 105, the system branches to a set of instructions indicated by process block 111. These instructions right justify the animal identification number in the B and C registers and the animal activity number in the D register. As indicated by process block 112, bit one of the status register 98 is then set to one to indicate that a complete transmission has occurred. The animal identification number is then stored in the random access memory 85 at a location 113 and the activity number is similarly stored in the random access memory 85 at a location 114. The system then returns through process blocks 104 and 97.

Referring again to FIG. 3, when a complete transmission has occurred, bit one of the status register 98 has been set by the PIO interrupt service routine 92 and the system branches at decision block 103 to determine whether five successive, identical transmissions of the animal identification and activity numbers have occurred. More particularly, an instruction indicated by decision block 116 examines the contents of a transmission counter 120 to determine if this is the first successful data transmission. If it is, the system branches directly to a set of instructions indicated by process block 117, which transfers the ID number stored in register 113 to a previous ID number register 118 contained in the random access memory 85, and which transfers the activity number at location 114 to a previous activity number register 119. The transmission counter 120 is then incremented one count as indicated by process block 121 and it is then examined by instructions indicated by decision block 122 to determine if the fifth successful data transmission has occurred. If not, the system branches back to process block 91 to await the next interrupt from the PIO 20.

After subsequent complete transmissions of the animal identification number and the animal activity number have taken place as determined by decision block 103, the system branches to determine if the transmitted data is identical to previous data transmissions. More specifically, the newly received animal identification number is first compared with the previously received animal identification number stored in the register 118 by a set of instructions indicated by decision block 123. If they are identical, the system proceeds to a second set of instructions indicated by decision block 124 which compares the newly received animal activity number with the previous activity number stored in the register 119. If either one of these two numbers does not identically compare, the system branches to a set of instructions indicated by process block 125 which reset the transmission counter to zero and loops back to process block 91 to await the next interrupt from the PIO 20. That is, when a transmission error has occurred, the system is reset so that the entire process is repeated.

When five successive identical transmissions of the animal identification number and the animal activity number have occurred, as determined by the decision block 122, the numbers are presumed accurate and the system branches at decision block 122 to instructions indicated by process blocks 126, 127 and 128 which output these numbers to the printer 7. More specifically, instructions indicated by process block 126 first subtract the activity number from the activity number which was transmitted when the animal's transponder was previously interrogated. It will be recalled that the fourteen-bit binary counter 69 in the transponder unit is not reset after each successful transmission, and hence, it is the difference between the last reading and the present reading which is of value in measuring the animal's activity. This calculated activity number as well as the animal identification number are then converted to BCD digits and are loaded into a print buffer as indicated by process block 127. A printer driver routine is then called to output these digits in the proper order and format to the printer 7.

It should be apparent that numerous variations can be made from the preferred embodiment of the invention described herein. A microprocessor based transceiver is preferred because it is an inexpensive and reliable means of making the needed calculations and performing the error detection functions. However, hardwired circuits could also be employed. Also, the time multiplexed transmissions of 3-bit bytes of the animal identification number and animal activity number is desirable because of the large number of animals which are to be identified. If fewer animals, for example sixteen, were involved, a single ten-bit presettable counter in the transponder could be loaded with the six-bit activity number and a four-bit identification number. This number might then be transmitted all at once back to the transceiver when interrogated. When larger animal identification numbers are required, however, it takes too long to count down the resulting large presettable counter. By breaking down the numbers into bytes which are sequentially transmitted to the transceiver and reassembled, the time needed to communicate both numbers is shortened considerably. This allows the animal transponder to be interrogated many times as it passes the transceiver coils and this in turn enables the use of redundant transmissions as a means of eliminating erroneous data.

COMPONENT APPENDIX

| Reference No. | Manufacturer And Model No. | Description |
|---|---|---|
| 7 | Centronics Microprinter-S1 | Alpha-numeric printer. |
| 10 | | See oscillator 20 in my co-pending U.S. patent application. |
| 11 & 12 | Motorola MC14024 | Seven-stage ripple counter. |
| 13 | | See a.c. amplifier 31 in my copending U.S. patent application. |
| 18 | Motorola MC14024 | Seven-stage ripple counter. |
| 20 | Zilog MK3881 | Z-80 parallel I/O controller. |
| 23 | | See amplifier and detector 45 in my copending U.S. patent application. |
| 27 | Motorola MC14528 | Monostable multivibrator. |
| 37 | Motorola MC14526 | Four-bit presettable counter. |
| 49 | Motorola MC14017 | Decade counter/divider. |
| 54 | Motorola MC14053 | Data selector/multiplexer. |
| 69 | Motorola MC14020 | Fourteen-bit binary counter. |
| 73 | MICRO SWITCH AS 408 PO | Mercury switch. |
| 83 | Intel Corporation 2758 | Two 1Kx8 UV erasable low power PROM. |
| 84 | Zilog Z-80 | Eight-bit microprocessor. |
| 85 | Fairchild 3539 | Two 256x8 MOS random access memory. |
| 86 | Zilog | Z-80 serial I/O controller. |
| 87 | Motorola MC1488 | RS-232-C line driver. |

APPENDIX A

```
;ABSOLUTE RAM ADDRESSES OR DATA
OFFSET:   EQU    -1000H
INTPT:    EQU    03H
PRT:      EQU    0800H
IDAK:     EQU    0802H
ADATA:    EQU    1800H
BUFRTP:   EQU    1810H
MIN:      EQU    1812H
HR:       EQU    1813H
DAY:      EQU    1814H
MON:      EQU    1815H
IDA:      EQU    181AH
ACTA:     EQU    181EH
COW:      EQU    1830H
ACTIV:    EQU    1832H
DOOR:     EQU    1834H
DATA:     EQU    1836H
COWBIN:   EQU    1838H
ACTBS:    EQU    1840H
BUFRBS:   EQU    2000H
STACK:    EQU    20FFH
```

```
; RELATIVE RAM ADDRESSES
STAT:       EQU         00H
GPCONT:     EQU         01H
ID:         EQU         02H
PRID:       EQU         04H
ACT:        EQU         06H
PRACT:      EQU         07H
IDCT:       EQU         08H
PRCOW:      EQU         0AH
VECT20:     EQU         0F0H
VECT28:     EQU         0F8H
VECT2A:     EQU         0FAH
VECT34:     EQU         0FCH
; ASCII CHARACTER DEFINITION
CR:         EQU         0DH
LF:         EQU         0AH
RS:         EQU         1EH
; INITIALIZATION
START:      LD          IX,ADATA
            LD          IY,BDATA
            LD          SP,STACK
            LD          HL,ADATA
            LD          DE,ADATA+1
            LD          BC,511D
            LD          (HL),00H
            LDIR                    ; SET ALL RAM TO 00H
            LD          A,INTPT
            LD          I,A         ; LOAD INTERRUPT TABLE POINTER
            LD          HL,BUFRBS
            LD          (BUFRTP),HL ; INITIALIZE TOP OF BUFFER
; INITIALIZATION OF SIO CHANNEL B.
; PORT 32H = DATA
; PORT 33H = COMMAND
; ASYCHRONOUS FORMAT, 7 BIT CHARACTER, 1 PARITY BIT, 2 STOP BITS
            LD          HL,SIO35+OFFSET ; LOAD DATA POINTER
            LD          C,33H       ; LOAD PORT POINTER
            LD          B,10D       ; LOAD COUNTER
            OTIR                    ; INITIALIZE SIO, CHANNEL B
; INITILIZATION OF PIO CHANNEL A AND B
; PORT 28H = DATA, PORT 29H = COMMAND (DOOR A)
; PORT 2AH = DATA, PORT 2BH = COMMAND (DOOR B)
            LD          A,4FH       ; SET TO INPUT MODE
            OUT         29H,A
            OUT         2BH,A
            LD          A,87H       ; ENABLE INTERRUPT
            OUT         29H,A
            OUT         2BH,A
            LD          A,VECT28    ; LOAD INTERRUPT VECTOR
            OUT         29H,A
            LD          A,VECT2A    ; LOAD INTERRUPT VECTOR
            OUT         2BH,A
; PRINT HEADING FOR DATA
            CALL        PRT
            CALL        IDAK
HALT:       IM          2
            EI
            HALT
            BIT         1,(IX+STAT) ; IF BIT 1 OF STATUS REG.=1
            CALL        NZ,CHKA+OFFSET ; THEN COMPARE PRESENT
                                    ; ID WITH PREVIOUS ID
            JR          HALT
; PIO INTERRUPT SERVICE ROUTINE
; INPUT ONE BYTE WHICH CONTAINS THREE BITS OF INFORMATION
; CHECK FOR ERRORS
; ASSEMBLE THREE BIT CODE
;
DRA:        DI          ; DISABLE ALL INTERRUPTS
```

```
              EXX           ; EXCHANGE BC, DE, HL
              EX       AF,AF'   ; EXCHANGE AF
              IN       A,(28H) ; INPUT BYTE
              BIT      0,(IX+STAT)
              JR       NZ,DRA1 ; JUMP IF BIT 0=1, FLAG BYTE HAS
                               ; BEEN DETECTED
              CP       07H     ; CHECK IF THIS IS THE FLAG BYTE
              JR       NZ,DRARET       ; JUMP IF A NOT EQUAL TO 7
    DRA5:     SET      0,(IX+STAT)     ; BIT 0=1, FLAG BYTE IS
                                       ; DETECTED
              LD       (IX+GPCONT),00H ; SET BYTE COUNTER = 0
              JR       DRARET
    DRA1:     CP       A,10H   ; IF A>15
              JP       P,DRA2+OFFSET   ; THEN AN ERROR HAS OCCURRED
              CP       07H
              JR       Z,DRA5  ; JUMP IF A=7, THIS IS A FLAG BYTE
              JP       M,DRA2+OFFSET   ; JUMP IF A<7, AN ERROR
                                       ; HAS OCCURRED
              PUSH     AF      ; SAVE THE ACCUMULATOR IN THE STACK
              LD       A,(IX+GPCONT)   ;
              CP       06H
              JR       Z,DRA4  ; JUMP IF GPCONT = 06, ONE CYCLE
                               ; IS COMPLETE
              CP       04H
              JP       P,DRA3+OFFSET   ; JUMP IF GPCONT>4, DATA IS
                                       ; ACTIVITY DATA
              INC      (IX+GPCONT)     ; INCREMENT BYTE COUNTER
              POP      AF      ; RECALL THREE BITS OF DATA
    ; ASSEMBLE ID CODE IN BC REGISTER PAIR
              SRL      A       ; BIT 0 TO CARRY
              RR       B       ; CARRY TO BIT 7 OF B
                               ; BIT 0 OF B TO CARRY
              RR       C       ; CARRY TO BIT 7 OF C
              SRL      A       ; REPEAT FOR BIT 1
              RR       B
              RR       C
              SRL      A       ; REPEAT FOR BIT 2
              RR       B
              RR       C
              JR       DRARET
    ; ASSEMBLE ACTIVITY CODE IN REGISTER D
    DRA3:     INC      (IX+GPCONT)     ; INCREMENT BYTE COUNTER
              POP      AF      ; RECALL THREE BITS OF DATA
              SRL      A       ; BIT 0 TO CARRY
              RR       D       ; CARRY TO BIT 7 OF D
              SRL      A       ; REPEAT FOR BIT 1 OF DATA
              RR       D
              SRL      A       ; REPEAT FOR BIT 2 of DATA
              RR       D
              JR       DRARET
    ; FINAL SHIFT OF ID AND ACTIVITY CODES
    DRA4:     POP      AF      ; REPOSITION STACK POINTER
              SRL      B       ; SHIFT BC ONE BIT RIGHT
              RR       C
              SRL      B       ; REPEAT
              RR       C
              SRL      B       ; REPEAT
              RR       C
              SRL      B       ; REPEAT
              RR       C
              SRL      D       ; SHIFT D ONE BIT RIGHT
              SRL      D       ; REPEAT
              SET      1,(IX+STAT)     ; BIT 1=1, DATA ASSEMBLED
                                       FOR COMPARISON
              LD       (ADATA+ID),BC   ; PLACE ID AND
                                       ; ACTIVITY IN RAM
              LD       (IX+ACT),D
    DRA2:     RES      0,(IX+STAT)     ; RESET FLAG BYTE
                                       ; DETECTED BIT
```

```
DRARET:     EXX             ; RECALL BC, DE, HL
            EX      AF,AF'  ; RECALL AF
            RETI
; CLOCK ADVANCE ROUTINE
CLK:        DI
            CALL    INCMIN+OFFSET
            CP      00H         ; IF MIN = 00
            JR      NZ,CLK1     ; THEN, INCREMENT HR
            CALL    INCHR+OFFSET
            SET     7,B         ; BIT 7=1, PRINT HEADING
            CP      00H         ; IF HR = 00
            JR      NZ,CLK1     ; THEN, INCREMENT DAY
            CALL    INCDAY+OFFSET
            CP      01H         ; IF DAY = 01
            JR      NZ,CLK1     ; THEN, INCREMENT MON
            CALL    INCMON+OFFSET
CLK1:       BIT     7,B         ; IF BIT 7=1
            JR      Z,CLKRET    ; THEN DO NOT PRINT HEADING
            CALL    PRT
CLKRET:     RETI
; MINUTE INCREMENT ROUTINE
INCMIN:     LD      A,(MIN)
            ADD     01H         ; MIN = MIN + 1
            DAA
            CP      60H
            JR      NZ,MIN1     ; IF MIN = 60
            XOR     A           ; THEN MIN = 00
MIN1:       LD      (MIN),A
            RET
; HOUR INCREMENT ROUTINE
INCHR:      LD      A,(HR)
            ADD     01H         ; HR = HR + 1
            DAA
            CP      24H
            JR      NZ,HR1      ; IF HR = 24,
            XOR     A           ; THEN HR = 00
HR1:        LD      (HR),A
            RET
; DAY INCREMENT ROUTINE
INCDAY:     LD      A,(DAY)
            ADD     01H         ; DAY = DAY + 1
            DAA
            CP      32H
            JR      NZ,DAY1     ; IF DAY = 32,
            LD      A,01H       ; THEN DAY = 01
DAY1:       LD      (DAY),A
            RET
; MONTH INCREMENT ROUTINE
INCMON:     LD      A,(MON)
            ADD     01H         ; MON = MON + 1
            DAA
            CP      13H
            JR      NZ,MON1     ; IF MON = 13,
            LD      A,01H       ; THEN MON = 01
MON1:       LD      (MON),A
            RET
; COMPARE PREVIOUS ID AND ACT WITH PRESENT ID AND ACT
CHKA:       RES     1,(IX+STAT)         ; CLEAR DATA READY BIT
                                        ; IN STATUS REG.
            LD      HL,(ADATA+PRID)     ; GET ID NUMBER
            LD      DE,(ADATA+ID)       ; GET PREVIOUS ID NUMBER
            XOR     A
            SBC     HL,DE               ; IF ID = PRID
            LD      (ADATA+PRID),DE     ; PRID = ID
            JR      NZ,CHKA1            ; THEN COMPARE ACTIVITY
                                        ; NUMBER
            LD      A,(IX+ACT)          ; GET ACTIVITY NUMBER
```

```
            LD      B,(IX+PRACT)        ; GET PREVIOUS ACTIVITY NUMBER
            CP      B                   ; IF ACT = PRACT
            LD      (ADATA+PRACT),A     ; PRACT = ACT
            JR      NZ,CHKA1            ; THEN THE TWO DATA ARE
                                        ; IDENTICAL
            LD      HL,(ADATA+IDCT)
            INC     HL                  ; IDCT = IDCT + 1
            LD      (ADATA+IDCT),HL
            LD      DE,0004H
            XOR     A
            SBC     HL,DE               ; IF IDCT = 0004,
            JR      NZ,CHKA2            ; THEN DISPLAY AND PRINT
                                        ; DATA
            LD      HL,(ADATA+PRID)
            LD      DE,(ADATA+PRCOW)
            XOR     A
            SBC     HL,DE    ; IF SAME COW HAS BEEN RE-IDENTIFIED,
            JR      Z,CHKA2  ; THEN DO NOT PRINT ID AND ACTIVITY
            LD      HL,(ADATA+PRID)     ; GET PRID FOR CONVERSION
            LD      (ADATA+PRCOW),HL    ; SAVE COW NUMBER
            LD      (COWBIN),HL         ; SAVE FOR ACTIVITY
                                        ; CALCULATION
            LD      DE,IDA              ; GET RESULTS POINTER
            CALL    BCD+OFFSET          ; CONVERT TO FOUR BCD DIGITS
            LD      H,00H
            LD      L,(IX+PRACT)        ; GET PRACT FOR CONVERSION
            LD      DE,ACTA             ; GET RESULTS POINTER
            CALL    BCD+OFFSET          ; CONVERT TO FOUR BCD DIGITS
            CALL    DISP+OFFSET
            LD      HL,(ACTA)           ; GET 'A' ACTIVITY READING
            LD      (DATA),HL           ; MOVE ACTIVITY READING FOR
                                        ; PRINTOUT
            LD      HL,(IDA)
            LD      (COW),HL            ; MOVE ID FOR PRINT OUT
            LD      A,'A'
            LD      (DOOR),A            ; LOAD 'A' FOR PRINT OUT
            CALL    ACTIVE+OFFSET
            CALL    IDAK
CHKA2:      RET
CHKA1:      LD      HL,0000H
            LD      (ADATA+IDCT),HL     ; IDCT = 0000
            RET
; COMPUTE ACTIVITY AND SAVE IN RAM
ACTIVE:     LD      DE,ACTBS            ; LOAD BASE ADDRES OF
                                        ; ACTIVITY TABLE
            LD      HL,(COWBIN)         ; RECALL COW NUMBER
                                        ; ( 0 < ID < 192 )
            ADD     HL,DE
            LD      A,(DATA)            ; RECALL PRESENT READING
            LD      B,(HL)   ; GET PREVIOUS READING
            LD      (HL),A   ; SAVE PRESENT READING
            CP      B        ; IF A < B
            JP      M,ACT2+OFFSET       ; THEN ADJUST TO OBTAIN
                                        ; POSITIVE RESULTS
ACT1:       SUB     B
            DAA
            LD      (ACTIV),A           ; SAVE ACTIVITY FOR PRINT OUT
            RET
ACT2:       ADD     A,64H
            DAA
            JR      ACT1
; END OF ROUTINE
; INTERRUPT DRIVEN PRINT ROUTINE
PRINT:      DI
            RES     0,(IX+STAT)
            RES     0,(IY+STAT)         ; RESET START GROUP
                                        ; DETECTED BITS
            LD      DE,BUFRBS           ; LOAD POINTER-BUFFER
                                        ; BASE
            LD      A,(DE)   ; GET ASCII CHARACTER
```

```
                CP          '$'         ; IF A = '$'
                JR          Z,PRTRET    ; THEN DISABLE SIO AND
                                        ; RETURN
                OUT         (32H),A     ; OUTPUT CHARACTER
                LD          HL,BUFRBS+1 ; LOAD POINTER
                LD          BC,(BUFRTP)
                DEC         BC          ; DECREMENT TOP OF BUFFER
                LD          (BUFRTP),BC
                LD          BC,160D     ; LOAD LENGTH OF CHARACTER BUFFER
                LDIR                    ; SHIFT ALL CHARACTERS IN BUFFER
                                        ; DOWN ONE LOCATION
                RETI
PRTRET:         LD          BC,BUFRBS
                LD          (BUFRTP),BC ; RESET TOP OF BUFFER
                                        ; AT BASE OF BUFFER
                LD          A,28H
                OUT         (33H),A     ; RESET TRANSMITT INTERRUPT PENDING
                RETI
; CONVERT 16 BIT BINARY NUMBER IN HL TO FOUR BCD DIGITS.
; DE CONTAINS THE ADDRESS AT WHICH THE BCD NUMBER IS TO BE
; STORED
BCD:            LD          B,02        ; LOAD LOOP COUNTER
                LD          C,10D       ; LOAD DIVISOR
BCD1:           CALL        DIV+OFFSET
                EX          DE,HL
                RRD                     ; BCD DIGIT TO RAM
                EX          DE,HL
                CALL        DIV+OFFSET
                EX          DE,HL
                RRD                     ; BCD DIGIT TO RAM
                EX          DE,HL
                INC         DE          ; ADVANCE MEMORY POINTER
                DJNZ        BCD1        ; DECREMENT LOOP COUNTER
                RET
; 16 BIT UNSIGNED DIVIDE ROUTINE
; HL = HL / C, A = REMAINDER
DIV:            PUSH        BC
                XOR         A
                LD          B,17D       ; LOAD LOOP COUNTER
                JR          DIVST
DIVLP:          SUB         C
                JP          P,DIVRES+OFFSET ; JUMP IF NO RESTORE
                ADD         C
DIVST:          ADD         HL,HL       ; SHIFT HL LEFT ONE BIT
                RLA
                JR          DIVCON
DIVRES:         ADD         HL,HL       ; SHIFT HL LEFT ONE BIT
                RLA
                INC         HL
DIVCON:         DJNZ        DIVLP       ; DECREMENT LOOP COUNTER
                RRA                     ; RESTORE REMAINDER
                POP         BC
                RET
INP:            DI
                LD          A,0E0H
                OUT         35H,A       ; END INTERRUPT
                LD          A,50H
                OUT         35H,A       ; READ SENSOR RAM AT DIGIT 0 WITH
                                        ; AUTO INCREMENT
                IN          A,(34H)     ; INPUT CLOCK ADVANCE SIGNALS
                LD          B,A         ; SAVE SWITCH STATUS
                BIT         4,B
                CALL        NZ,INCMIN+OFFSET
                BIT         5,B
                CALL        NZ,INCHR+OFFSET
                BIT         6,B
                CALL        NZ,INCDAY+OFFSET
                BIT         7,B
```

```
                CALL       NZ,INCMON+OFFSET
                CALL       DISP+OFFSET
                RETI
SIO35:          DB         02H       ; POINTER SET TO REGISTER 2B
                DB         VECT34    ; LOAD INTERRUPT VECTOR
                DB         03H       ; POINTER SET TO REGISTER 3B
                DB         40H       ; RECEIVER DISABLED
                DB         04H       ; POINTER SET TO REGISTER 4B
                DB         0CH       ; NO PARITY, 2 STOP BIT, X1
                                     ; CLOCK, ASYNCHRONOUS MODE
                DB         05H       ; POINTER SET TO REGISTER 5B
                DB         28H       ; 7 BITS PER CHARACTER, TRANS-
                                     ; MITTER ENABLED
                DB         01H       ; POINTER SET TO REGISTER 1B
                DB         02H       ; INTERRUPT ENABLED
; CREATE INTERRUPT TABLE FOR PIO AND SIO
                ORG        1300H+VECT28
                DW         DRA+OFFSET, DRB+OFFSET, PRINT+OFFSET,
                           START+OFFSET
                END        START
```

I claim:

1. An estrus detection system for an animal, the combination comprising:
a transponder unit mounted to the animal, and including
 (a) a motion sensing device which provides an electrical signal in response to animal movement,
 (b) a counter coupled to said motion sensing device to receive said electrical signals and store a number which is indicative of the number of animal movements, and
 (c) means responsive to an interrogation signal for transmitting data indicative of the number stored in said counter;
a transceiver unit positioned near a location which the animal frequents, said transceiver unit including
 (d) means for generating an interrogation signal to said transponder unit,
 (e) means for receiving the data transmitted by said transceiver unit,
 (f) means coupled to said receiving means for converting said received data into an activity number which is indicative of the number of animal movements, and
 (g) means coupled to said converting means for displaying information which incorporates said activity number.

2. The estrus detection system as recited in claim 1 in which said transponder unit also includes means for transmitting data which identifies the animal to which it is attached and said transceiver unit converting means converts this data into an identification number and couples it to said display means.

3. The estrus detection system as recited in claims 1 or 2 in which said transponder unit is attached to the neck of the animal.

4. An animal identification and estrus detection system, the combination comprising:
a transponder unit mounted to the animal and including
 (a) a motion sensing device which provides an electrical signal in response to animal movement,
 (b) a counter coupled to said motion sensing device to receive said electrical signals and store an activity number which is indicative of the number of animal movements,
 (c) means for generating an animal identification number,
 (d) means responsive to an interrogation signal for transmitting data indicative of a number applied to its input terminal,
 (e) means coupled to said counter and said generating means for sequentially applying the identification number and the activity number to the input terminal of said transmitting means;
a transceiver unit positioned near a location which the animal frequents, said transceiver unit including
 (f) means for generating an interrogation signal to said transponder unit,
 (g) means for receiving the data transmitted by said transponder unit,
 (h) means coupled to said receiving means for converting said data into an activity number and an animal identification number, and
 (i) means coupled to said converting means for displaying the activity number and the animal identification number.

5. The animal identification and estrus detection system as recited in claim 4 in which said means for displaying the activity number and animal identification number includes a microprocessor coupled to said converting means by a data bus and a printer coupled to said microprocessor through said data bus.

6. The animal identification and estrus detection system as recited in claim 5 in which said microprocessor is programmed to repeatedly input said activity number and the animal identification number from said converting means, to compare successively received activity numbers and animal identification numbers, and to output said activity number and animal identification to said display when a preselected number of identical numbers are compared.

7. The animal identification and estrus detection system as recited in claim 4 in which said converting means includes a counter which is coupled to said interrogation signal generating means and said receiving means, said counter being incremented by said generating means and the contents of said counter being coupled to said display means in response to the data transmitted by said transponder unit.

8. A transponder unit for mounting to an animal and being responsive to an interrogation signal generated by a transceiver unit to generate a signal to said transceiver unit which indicates the identity of the animal to which the transponder unit is attached and which indicates the activity of the animal, the combination comprising:

a motion sensing device which provides an electrical signal in response to animal movement;

a counter coupled to said motion sensing device to receive said electrical signals and store a number which is indicative of the number of animal movements;

a presettable counter having an input connected to receive said interrogation signal, an output terminal connected to generate said signal to said transceiver unit and a set of present terminals;

means having inputs connected to said counter and outputs connected to said presettable counter preset terminals for coupling a number from said counter to said presettable counter when enabled;

means coupled to said presettable counter preset terminals for applying an identication number to said presettable counter when enabled; and means coupled to the output terminal of said presettable counter for sequentially enabling said last two named means.

9. An estrus detection system for an animal, the combination comprising:

a transponder unit mounted to the animal, and including (a) a motion sensing device which provides an electrical signal in response to animal movement, (b) accumulator means coupled to said motion sensing device to receive said electrical signals and store a signal which is indicative of the number of animal movements, and (c) means responsive to an interrogation signal and coupled to said accumulator means for transmitting data indicative of the number of animal movements;

a transceiver unit positioned near a location which the animal frequents, said transceiver unit including (d) means for generating an interrogation signal to said transponder unit, (e) means for receiving the data transmitted by said transceiver unit, (f) means coupled to said receiving means for converting said received data into an activity number which is indicative of the number of animal movements, and (g) means coupled to said converting means for displaying information which incorporates said activity number.

10. The estrus detection system as recited in claim 9 in which said transponder unit also includes means for transmitting data which identifies the animal to which it is attached and said transceiver unit converting means converts this data into an identification number and couples it to said display means.

* * * * *

UNITED STATES PATENT AND TRADEMARK OFFICE
CERTIFICATE OF CORRECTION

PATENT NO. : 4,247,758

DATED : January 27, 1981

INVENTOR(S) : James A. Rodrian

It is certified that error appears in the above—identified patent and that said Letters Patent is hereby corrected as shown below:

| | |
|---|---|
| Column 1, line 49 | "incudes" should be -- includes -- |
| Column 2, line 22 | "thereof" should be -- hereof -- |
| Column 9, line 13 | "flat" should be -- flag -- |
| Column 23, line 41 | "transceiver" should be -- transponder -- |
| Column 25, line 12 | "present" should be -- preset -- |
| Column 26, line 14 | "transceiver" should be -- transponder -- |

Signed and Sealed this

Twenty-ninth Day of September 1981

[SEAL]

Attest:

Attesting Officer

GERALD J. MOSSINGHOFF

Commissioner of Patents and Trademarks